(12) United States Patent
Lenox et al.

(10) Patent No.: US 7,579,598 B2
(45) Date of Patent: Aug. 25, 2009

(54) REALTIME LINE OF RESPONSE POSITION CONFIDENCE MEASUREMENT

(75) Inventors: Mark W. Lenox, Harriman, TN (US); Blake Atkins, Maryville, TN (US); Danny F Newport, Knoxville, TN (US); Aaron McFarland, Knoxville, TN (US); Stefan Siegel, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/759,163

(22) Filed: Jun. 6, 2007

(65) Prior Publication Data
US 2007/0290140 A1    Dec. 20, 2007

Related U.S. Application Data

(60) Provisional application No. 60/811,189, filed on Jun. 6, 2006.

(51) Int. Cl.
*G01T 1/164* (2006.01)

(52) U.S. Cl. .................................. 250/363.03

(58) Field of Classification Search .. 250/363.01–362.1
See application file for complete search history.

(56) References Cited

OTHER PUBLICATIONS

Jeong et al., "Performance improvement of small gamma camera using NaI(TI) plate and position sensitive phto-multiplier tubes,", 2004, Phys. Med. Biol., vol. 49, pp. 4961-4970.*
Stonger et al. "Optimal calibration of PET crystal position maps using gaussian mixture models,", 2004, IEEE Transactions on Nuclear Science, vol. 51, No. 1. pp. 85-90.*

* cited by examiner

*Primary Examiner*—David P Porta
*Assistant Examiner*—Kiho Kim

(57) ABSTRACT

A PET event position calculation method using a combination angular and radial event map wherein identification of the radial distance of the event from the centroid of the scintillation crystal with which the event is associated as well as angular information is performed. The radial distance can be converted to a statistical confidence interval, which information can be used in downstream processing. More sophisticated reconstruction algorithms can use the confidence interval information selectively, to generate higher fidelity images with higher confidence information, and to improve statistics in dynamic imaging with lower confidence information.

12 Claims, 4 Drawing Sheets

REALTIME LINE OF RESPONSE POSITION CONFIDENCE MEASUREMENT

CLAIM OF PRIORITY FROM RELATED APPLICATION

This application claims priority under 35 U.S.C. § 119(e) from copending Provisional Application Ser. No. 60/811,189, filed Jun. 6, 2006.

FIELD OF THE INVENTION

The present invention generally relates to positron emission tomography (PET), and in particular to improvement in the spatial resolution of PET images reconstructed from acquisition data obtained from PET block detectors.

BACKGROUND OF THE INVENTION

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by a scintillation crystal, with which the photons interact to produce flashes of light or "events." Events are detected by an array of photodetectors, such as photomultiplier tubes, and their spatial locations or positions are calculated and stored. In this way, an image of the organ or tissue under study is created from detection of the distribution of the radioisotopes in the body.

One particular nuclear medicine imaging technique is known as Positron Emission Tomography, or PET. PET is used to produce images for diagnosing the biochemistry or physiology of a specific organ, tumor or other metabolically active site. Measurement of the tissue concentration of a positron emitting radionuclide is based on coincidence detection of the two gamma photons arising from positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence event, they also identify a line of response, or LOR, along which the annihilation event has occurred.

An example of a PET method and apparatus is described in U.S. Pat. No. 6,858,847, which patent is incorporated herein by reference in its entirety. After being sorted into parallel projections, the LORs defined by the coincidence events are used to reconstruct a three-dimensional distribution of the positron-emitting radionuclide within the patient. PET is particularly useful in obtaining images that reveal bioprocesses, e.g. the functioning of bodily organs such as the heart, brain, lungs, etc. and bodily tissues and structures such as the circulatory system.

The PET apparatus includes a detector section constructed of blocks, each forming an array of scintillation crystals, a data acquisition section, and an event processing section. FIG. 1. shows an example of a data acquisition section applicable to the present invention. Analog front-end circuitry 101 (such as Application-Specific Integrated Circuits (ASICs)) connects to external detectors such as Photomultiplier Tubes (PMTs) or Avalanche Photodiodes (APDs) (not shown), which in turn are coupled to scintillation crystal blocks (not shown). Energy data in the form of analog signals are outputted from the analog front-end circuitry to Analog-to-Digital Converters (ADCs) 103, which convert the analog signals to digital data samples. The digital energy data samples outputted from the ADCs are passed to a Field Programmable Gate Array (FPGA) 105. For the Siemens Inveon® PET system, sixteen data samples are accumulated for each event initiated by a Constant Fraction Discriminator (CFD) trigger from the analog front-end circuitry.

In addition to the digital energy data samples, a digital time stamp with a 312 picosecond resolution is outputted from the analog front-end circuitry, which also is passed to the FPGA 105 and used in subsequent event processing. Once received by the FPGA, the digital data samples may be processed as needed for the particular application. The data samples may also be outputted from the FPGA for analysis and processing on a host machine in addition to subsequent processing within the FPGA.

FIG. 2 illustrates details of the FPGA 105. Various algorithms may be applied to the accumulated digital data samples within the FPGA for determining the optimum data representation of the event represented by the data samples. The selected algorithm is executed on the accumulated data samples by an Event Representation module 201. The resultant data representation of an event is then used by X,Y Calculation module 203 to calculate an X,Y spatial coordinate. The coordinate is subsequently used to address a Crystal Look-up Table (CLT) 209 that is implemented in a Flash memory device external to the FPGA. A crystal value is then outputted from the CLT 209 dependent upon the X,Y coordinate that addressed the CLT.

This crystal value is then fed back into the FPGA 105 and used to address an Energy Qualification and Time Correction look-up table (ELT) 205 implemented within the FPGA. ELT 205 stores upper and lower energy values and a time correction value for each crystal. This allows energy qualification and time correction to be applied to each individual crystal. Once a crystal event has been qualified as to energy and corrected as to timing based on the identified crystal in which the event occurred, the corrected data form a "Singles" event that is then placed into a FIFO buffer 207 for transmission over an I/O channel for subsequent processing, such as coincidence determination.

Prior to the present invention, crystal identification mapping was based on square or rectangular maps utilizing the entire X,Y area of the scintillation crystal array, as shown in FIG. 3. This technique provided a binary decision as to the position of the event based on the crystal data stored in the CLT, such that each event is mapped to a particular crystal and is assumed to have occurred at the centroid of the crystal. Because all events incident within the entire detector field of view are captured, the sensitivity of the detector is maximized. However, events detected as occurring on the boundary between two crystals could be mispositioned, depending on the peak/valley ratio of the given detector. This results in a statistical degradation of the resolution of the final image.

Circular or "island" mapping is also known in the art, wherein circular regions are formed around the centroids of the scintillation crystals. The use of smaller regions provides increased confidence that the detected event actually occurred in the specified crystal; however sensitivity is reduced because events that are detected as occurring in areas outside the circular regions are discarded. Further, the radius of the regions needs to be determined in advance, or unnecessary loss of sensitivity will result, as reduction of the radius of the circular regions at some point dramatically reduces the overall image quality because of the extreme loss of statistical data.

SUMMARY OF THE INVENTION

The present invention overcomes the drawbacks in the art by providing a PET event position calculation method using a combination angular and radial event map wherein identification of the radial distance of the event from the centroid of the scintillation crystal with which the event is associated as well as angular information is performed. The radial distance can be converted to a statistical confidence interval, which information can be used in downstream processing. More sophisticated reconstruction algorithms can use the confidence interval information selectively, to generate higher fidelity images with higher confidence information, and to improve statistics in dynamic imaging with lower confidence information.

DETAILED DESCRIPTION OF THE INVENTION

The present invention will now be described and disclosed in greater detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach one having ordinary skill in the art to make and use the invention.

Figure 1:
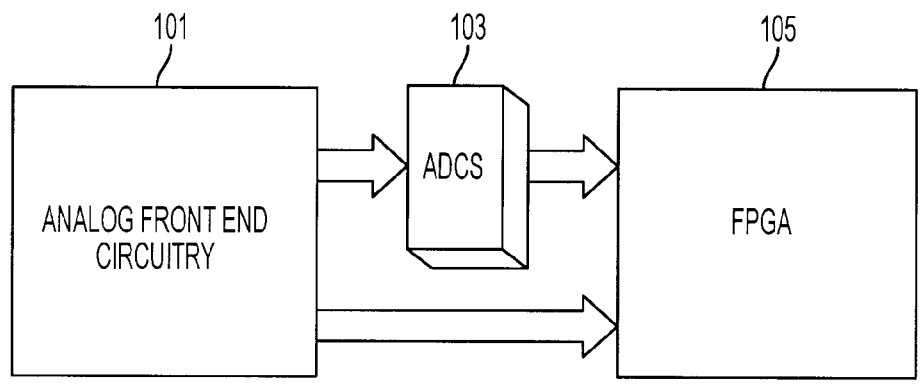
FIG. 1 is a block diagram of a data acquisition module of a PET system, which is applicable to the present invention.
Figure 2:
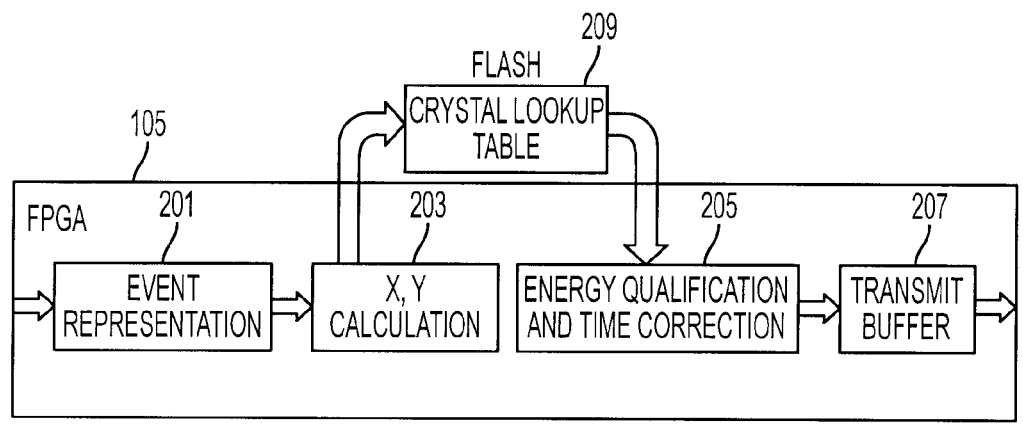
FIG. 2 is a block diagram of an event processing module of the FPGA of FIG. 1.
Figure 3:
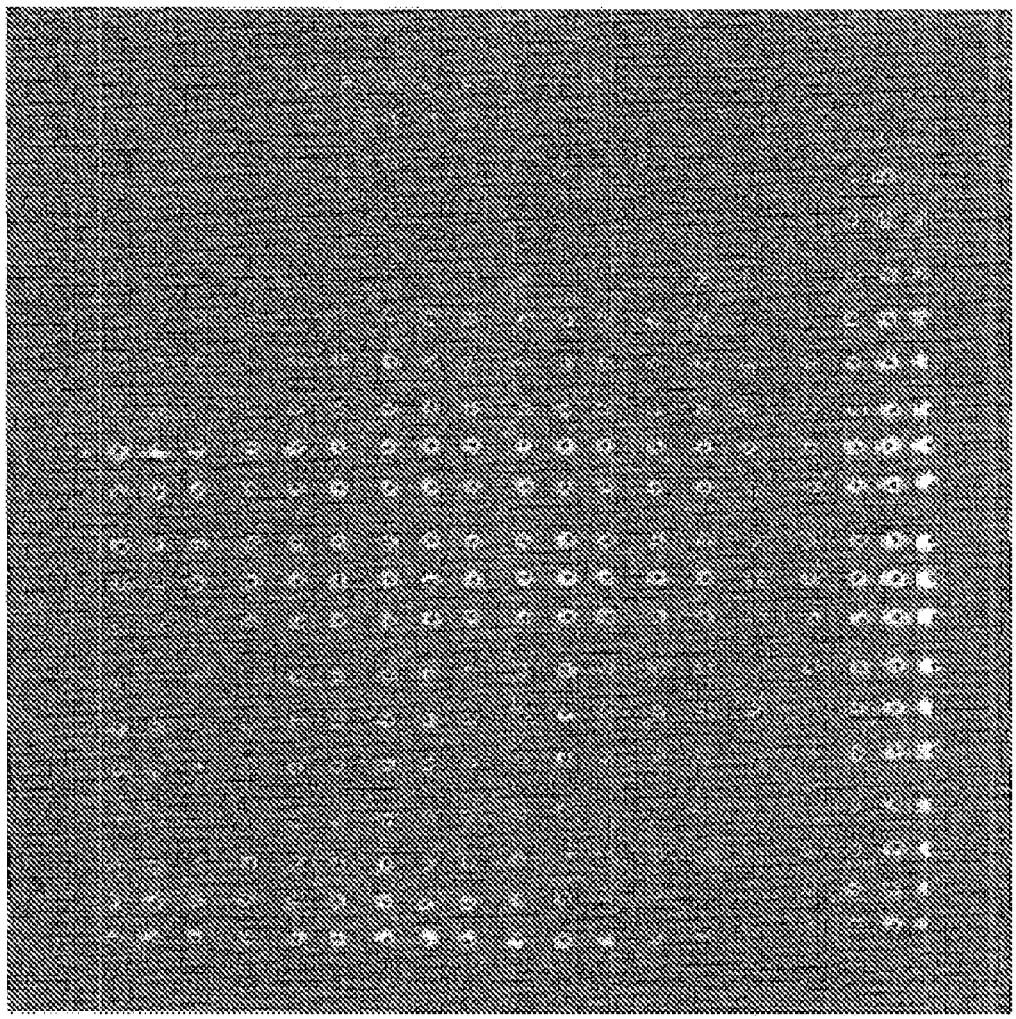
FIG. 3 is a diagram of a conventional square/rectangular crystal map used in PET imaging.
Figure 4:
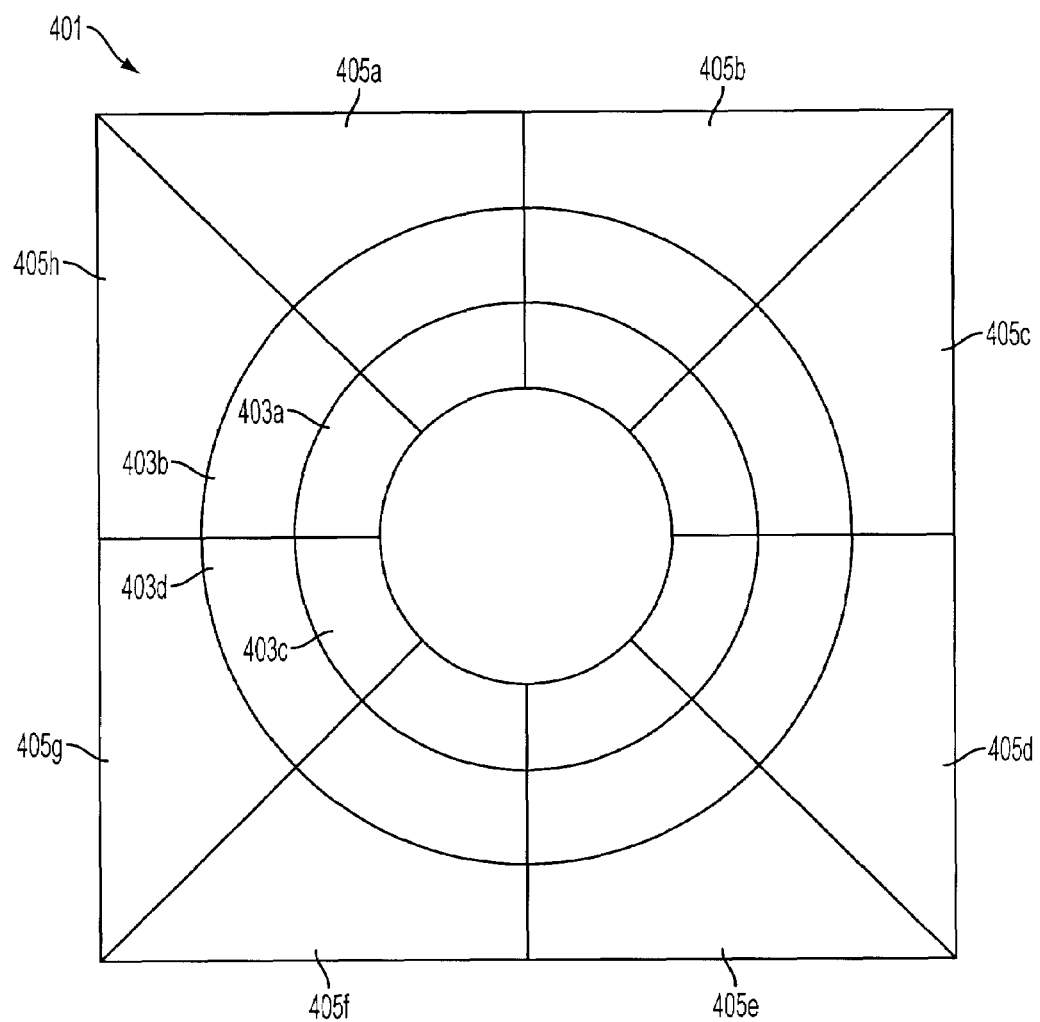
FIG. 4 shows a radial/angular crystal map for PET imaging in accordance with one embodiment of the present invention.

Referring to FIG. 4, in accordance with the invention a PET event mapping technique 401 is provided. The event positioning map 401 encodes the radial distance of the detected event from the centroid of the identified scintillation crystal, as well as angular information of the event in an X,Y quadrant system. The encoded radial data provides additional confidence information that can be used in downstream data processing, to optimize image quality. The map 401 can be square or rectangular, and sized to cover the entire crystal. As opposed to the conventional square map, the map 401 provides additional confidence level information that can be used to enhance image resolution or to improve statistics, depending on the application. As opposed to the conventional circular map, the map 401 captures all scintillation events. The map 401 can be electronically generated and stored in a memory such as flash memory CLT 209.

According to the embodiment as shown in FIG. 4, the confidence level of the event data is encoded in four radial zones: center region 403a and radial regions 403b, 403c and 403d, from the center to the edge of the map respectively. The radial direction of the event with respect to the centroid of the crystal is encoded in eight angular zones 405a-405h. This additional encoding results in 3 bits of angular information and 2 bits of radial distance information, or an additional 5 bits of event encoding information to be transmitted to downstream data processing. Additional zones or fewer zones may be provided in both directions, depending on the capabilities of the hardware. For example, the Siemens Quicksilver™ Event Processing Module allows up to 16 bits of crystal identification data. The Inveon® PET system has a 20×20 crystal block detector, requiring 9 bits (i e., 20×20=400 crystals, requiring $2^9$=512 or 9 bits to encode). Therefore, 7 additional bits are available to be allocated for radial and angular encoding in accordance with the invention.

By measuring the radial distance from the center of the crystal, a statistical measure can be formed of the level of confidence that the actual detected event was associated with the particular crystal centroid identified through consultation of the look-up table. The radial distance determined is converted to a confidence interval. Higher fidelity images can be obtained by using only events with a predetermined high confidence level, provided a statistically sufficient amount of event data is available. Conversely, lower confidence level events can be used to improve statistics where higher statistical accuracy is more important, such as in dynamic imaging applications.

Figure 5:
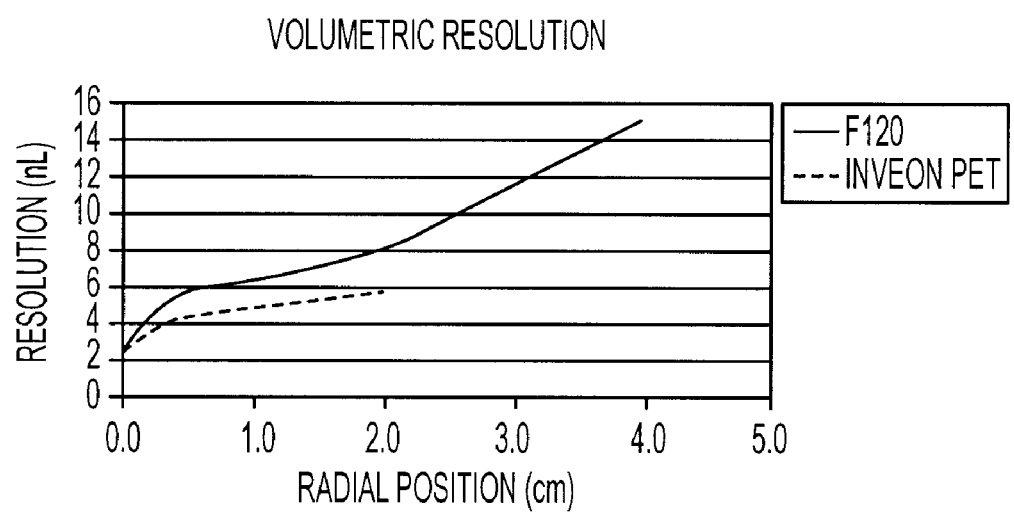
FIG. 5 is a graph comparing image resolution of PET images using the conventional crystal mapping technique with image resolution obtained by using the present invention.

FIG. 5 shows a comparison of the prior art crystal mapping scheme as used by an F120 PET system versus the radial and angular mapping technique as used by an Inveon® PET system in accordance with the present invention. These detectors have exactly the same pitch. As shown, improved image resolution across the field of view is achieved using the additional information provided by the present confidence interval-based lookup scheme.

It should be appreciated by those having ordinary skill in the art that while the present invention has been illustrated and described in what is deemed to be the preferred embodiments, various changes and modifications may be made to the invention without departing from the spirit and scope of the invention. Therefore, it should be understood that the present invention is not limited to the particular embodiments disclosed herein.

What is claimed is:

1. A method of encoding PET scintillation events incident on a scintillation crystal block detector array of a PET system, comprising:
   dividing scintillation crystals of said block detector array into a center region over a centroid of a scintillation crystal of a PET detector and a plurality of radial regions surrounding said center region;
   calculating position coordinates of a scintillation event incident on a crystal of said block detector array;
   mapping said calculated position coordinates to said regions;
   encoding said scintillation event with a predetermined identification code corresponding to the region to which said position coordinates are mapped.

2. The method of claim 1, wherein said regions are stored as a crystal map in an electronic storage medium.

3. The method of claim 1, further comprising the step of dividing said radial regions into a plurality of angular regions.

4. The method of claim 3, wherein said angular regions comprise at least eight regions.

5. The method of claim 1, wherein said radial regions comprise at least three regions.

6. The method of claim 1, wherein said radial regions extend over the entire area of a crystal.

7. An event processing module for a PET imaging system, comprising:
- a position coordinate calculator that calculates a pair of spatial position coordinates of a scintillation event incident on a scintillation crystal of said system;
- a look-up table storing information mapping spatial position coordinates to specific scintillation crystals of said system, said information including a center region over a centroid of each scintillation crystal of said PET system, and a plurality of radial regions surrounding said center region; and
- an encoder that encodes scintillation event data with information retrieved from said look-up table.

8. The event processing module according to claim 7, wherein said center and radial regions collectively form a square.

9. The event processing module according to claim 7, wherein said mapping information covers an entire area of said scintillation crystal.

10. The event processing module according to claim 7, wherein said plurality of radial regions comprise at least three regions.

11. The event processing module according to claim 7, wherein said mapping information further comprises a plurality of angular regions into which said plurality of radial regions are divided.

12. The event processing module according to claim 11, wherein said plurality of angular regions comprise at least eight regions.

* * * * *